(12) United States Patent
Shefi et al.

(10) Patent No.: US 7,850,720 B2
(45) Date of Patent: Dec. 14, 2010

(54) METHOD AND APPARATUS FOR APPLYING LIGHT THERAPY

(76) Inventors: Ron Shefi, 3430 N. Greenbrier Rd., Long Beach, CA (US) 90808; Peter Jungen, 119 1/2 N-Superior St., Albion, MI (US) 49224

( * ) Notice: Subject to any disclaimer, the term of this patent is extended or adjusted under 35 U.S.C. 154(b) by 239 days.

(21) Appl. No.: 11/901,726

(22) Filed: Sep. 18, 2007

(65) Prior Publication Data

US 2008/0077199 A1    Mar. 27, 2008

Related U.S. Application Data

(60) Provisional application No. 60/846,649, filed on Sep. 23, 2006.

(51) Int. Cl.
*A61N 5/06* (2006.01)
(52) U.S. Cl. .......................................... 607/88; 607/91
(58) Field of Classification Search .................. 607/88, 607/91; 351/123; 600/476
See application file for complete search history.

(56) References Cited

U.S. PATENT DOCUMENTS

| | | | | |
|---|---|---|---|---|
| 4,930,504 A | * | 6/1990 | Diamantopoulos et al. | 607/88 |
| 4,940,323 A | | 7/1990 | Downing | 351/203 |
| 5,500,009 A | * | 3/1996 | Mendes et al. | 607/88 |
| 5,545,192 A | * | 8/1996 | Czeisler et al. | 607/88 |
| 5,645,578 A | | 7/1997 | Daffer et al. | |
| 6,053,936 A | | 4/2000 | Koyama et al. | 607/88 |
| 6,221,095 B1 | * | 4/2001 | Van Zuylen et al. | 607/88 |
| 6,223,071 B1 | * | 4/2001 | Lundahl et al. | 600/476 |
| 6,488,698 B1 | | 12/2002 | Hyman | 607/91 |
| 6,811,563 B2 | | 11/2004 | Savage, Jr. et al. | 607/88 |
| 6,896,693 B2 | * | 5/2005 | Sullivan | 607/91 |
| 6,955,684 B2 | | 10/2005 | Savage, Jr. et al. | 607/88 |

(Continued)

OTHER PUBLICATIONS

PCT/US08/10816 International Search Report and Written Opinion.

(Continued)

*Primary Examiner*—Ahmed M Farah
(74) *Attorney, Agent, or Firm*—Clifford Kraft

(57) ABSTRACT

A method and apparatus for light therapy, which is a method using light for treating diseases and/or maintaining the health of a living organism. The method comprises delivering a light modulated at a specific frequency and intensity for a specified duration to the whole body or a portion of the body of the living organism. Disclosed herein are different sequences of light therapy useful for assisting the recovery from e.g., disease, injury, or malfunction. The improvement in health of the living organism after each treatment is observed. If necessary to increase the improvement in health, the sequence of light may be repeated in one session (such as two back-to-back sequences of treatment in one sitting in one day), and/or the organism may be treated over a period of time, such as receiving the sequence of light every 3 to 5 days, etc., until improvement is observed, the health problem is resolved, or a sense of improved well being is experienced by the treated organism. The living organism is preferably an animal, and is more preferably a human. Also described are devices and electronic systems for delivering such light therapy. Further described are methods for optimizing the light therapy. An electronic circuit supplies and controls timing, repetition rate, intensity and application of the light.

2 Claims, 5 Drawing Sheets

U.S. PATENT DOCUMENTS

| | | | |
|---|---|---|---|
| 7,534,255 B1 * | 5/2009 | Streeter et al. | 607/88 |
| 2001/0008973 A1 | 7/2001 | Van Zuylen et al. | |
| 2002/0029071 A1 * | 3/2002 | Whitehurst | 607/88 |
| 2002/0198575 A1 * | 12/2002 | Sullivan | 607/88 |
| 2003/0181961 A1 * | 9/2003 | Kamei | 607/88 |
| 2004/0044384 A1 * | 3/2004 | Leber et al. | 607/88 |
| 2004/0138727 A1 * | 7/2004 | Taboada et al. | 607/88 |
| 2004/0147984 A1 | 7/2004 | Altshuler et al. | |
| 2004/0249423 A1 * | 12/2004 | Savage | 607/88 |
| 2005/0237479 A1 * | 10/2005 | Rose | 351/123 |

OTHER PUBLICATIONS

PCT International Preliminary Report on Patentability Mar. 24, 2010, (PCT/US08/010816).

* cited by examiner

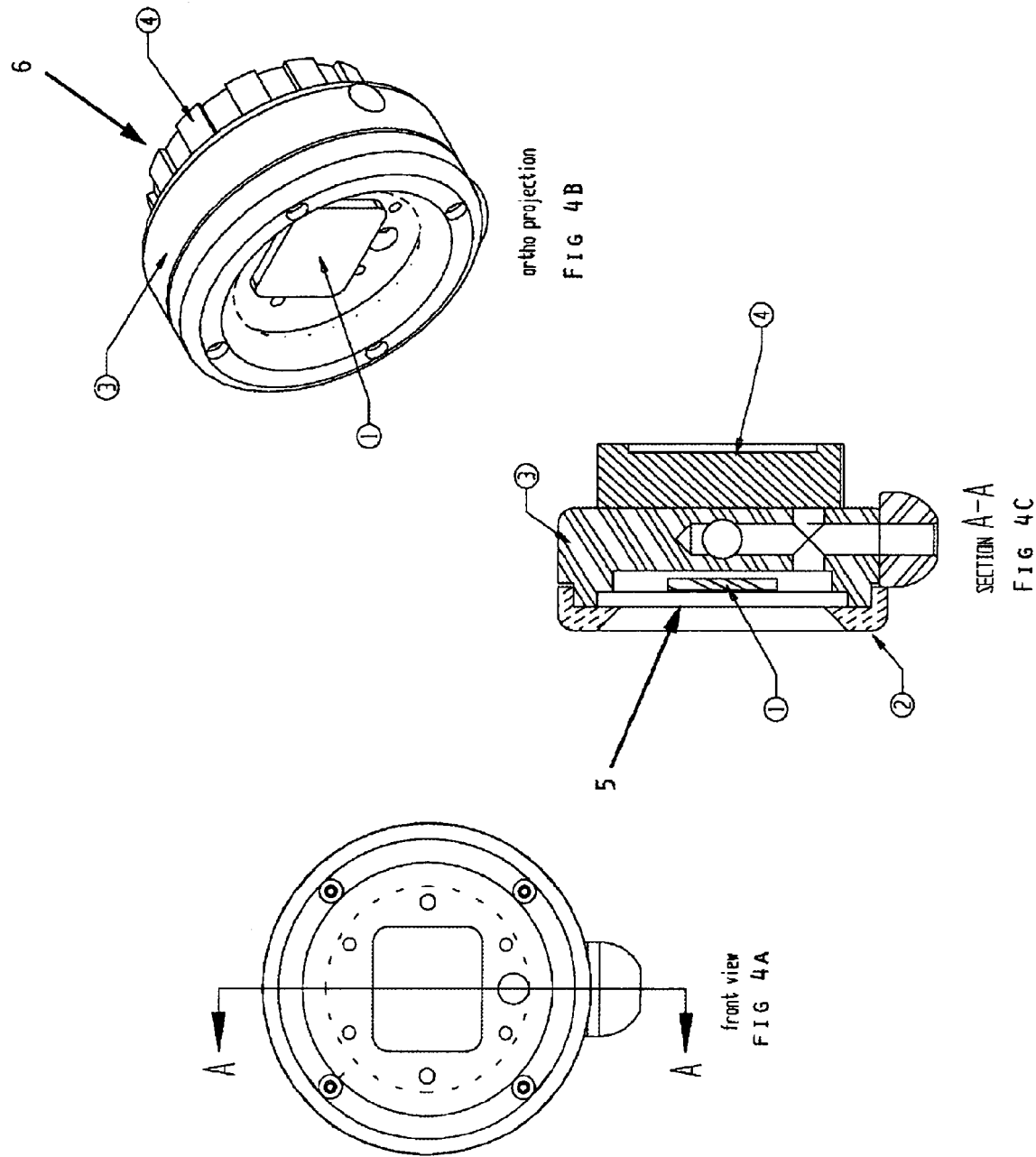

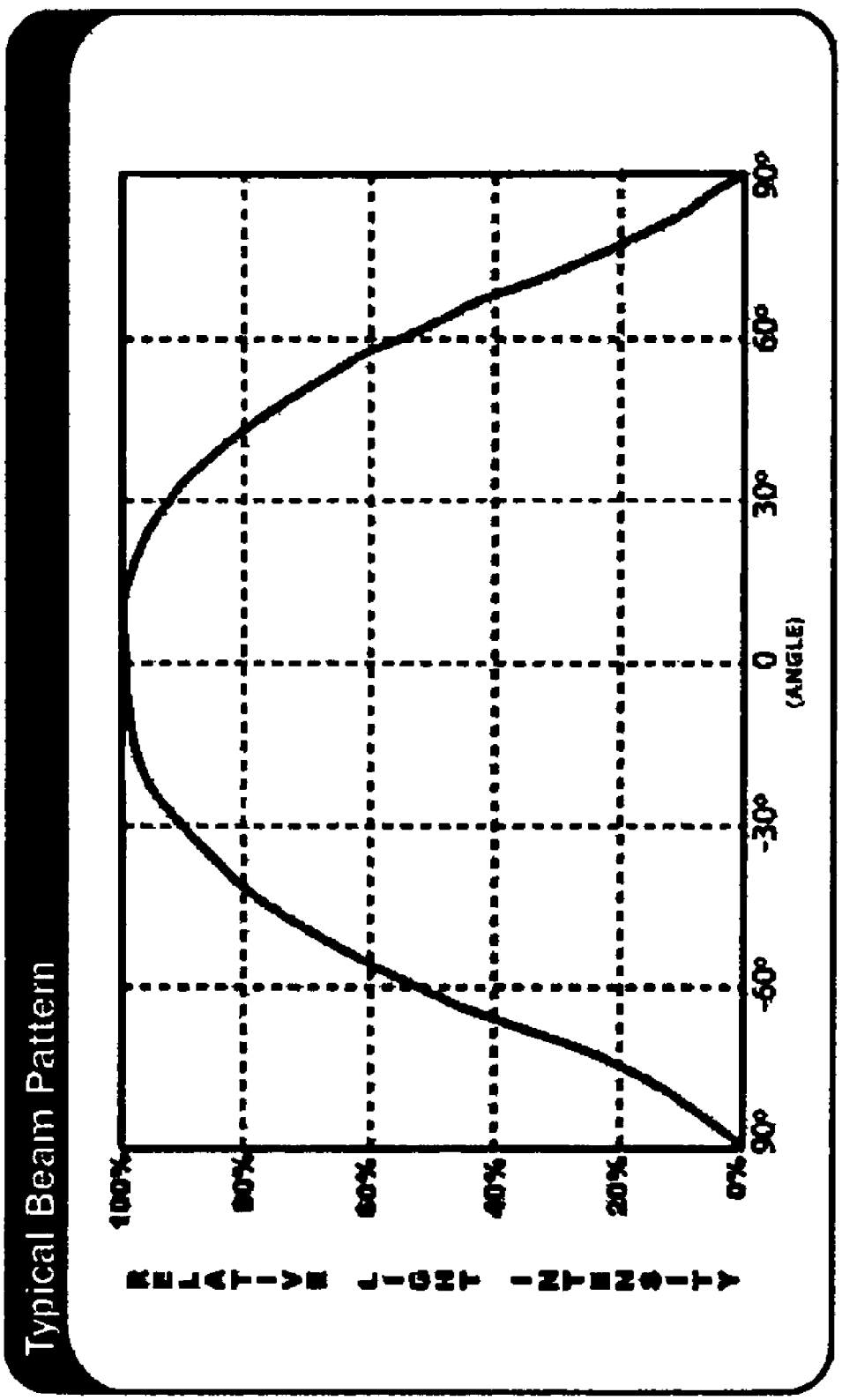
PRIOR ART FIG. 5

METHOD AND APPARATUS FOR APPLYING LIGHT THERAPY

This application is related to and claims priority from U.S. Provisional Patent application No. 60/846,649 filed Sep. 23, 2006. Application 60/846,649 is hereby incorporated by reference.

TECHNICAL FIELD OF THE INVENTION

The present invention relates to light therapy, and more particularly to using light for treating diseases and/or maintaining the health of a living organism.

SUMMARY OF THE INVENTION

The present invention relates to light therapy, which is a method using light for treating diseases and/or maintaining the health of a living organism. The method comprises delivering a light modulated at a specific frequency and intensity for a specified duration to the whole body or a portion of the body of the living organism. Disclosed herein are different sequences of light therapy useful for assisting the recovery from e.g., disease, injury, or malfunction. The improvement in health of the living organism after each treatment is observed. If necessary to increase the improvement in health, the sequence of light may be repeated in one session (such as two back-to-back sequences of treatment in one sitting in one day), and/or the organism may be treated over a period of time, such as receiving the sequence of light every 3 to 5 days, etc., until improvement is observed, the health problem is resolved, or a sense of improved well being is experienced by the treated organism. The living organism is preferably an animal, and is more preferably a human. Also described are devices and electronic systems for delivering such light therapy. Further described are methods for optimizing the light therapy. An electronic circuit supplies and controls timing, repetition rate, intensity and application of the light.

BRIEF DESCRIPTION OF THE DRAWINGS

FIGS. 4A, 4B and 4C present different views of one embodiment of the surface illuminating unit: the surface illuminating unit (6) of the Parkinson's Light Device (13): FIG. 4A showing the front view, FIG. 4B showing a projection view, in FIG. 4C is a sectional view along line A-A of FIG. 4A.

FIG. 5 is a graph of the typical beam pattern of prior art Lamina BL-3000 green LED array.

Figure 1:
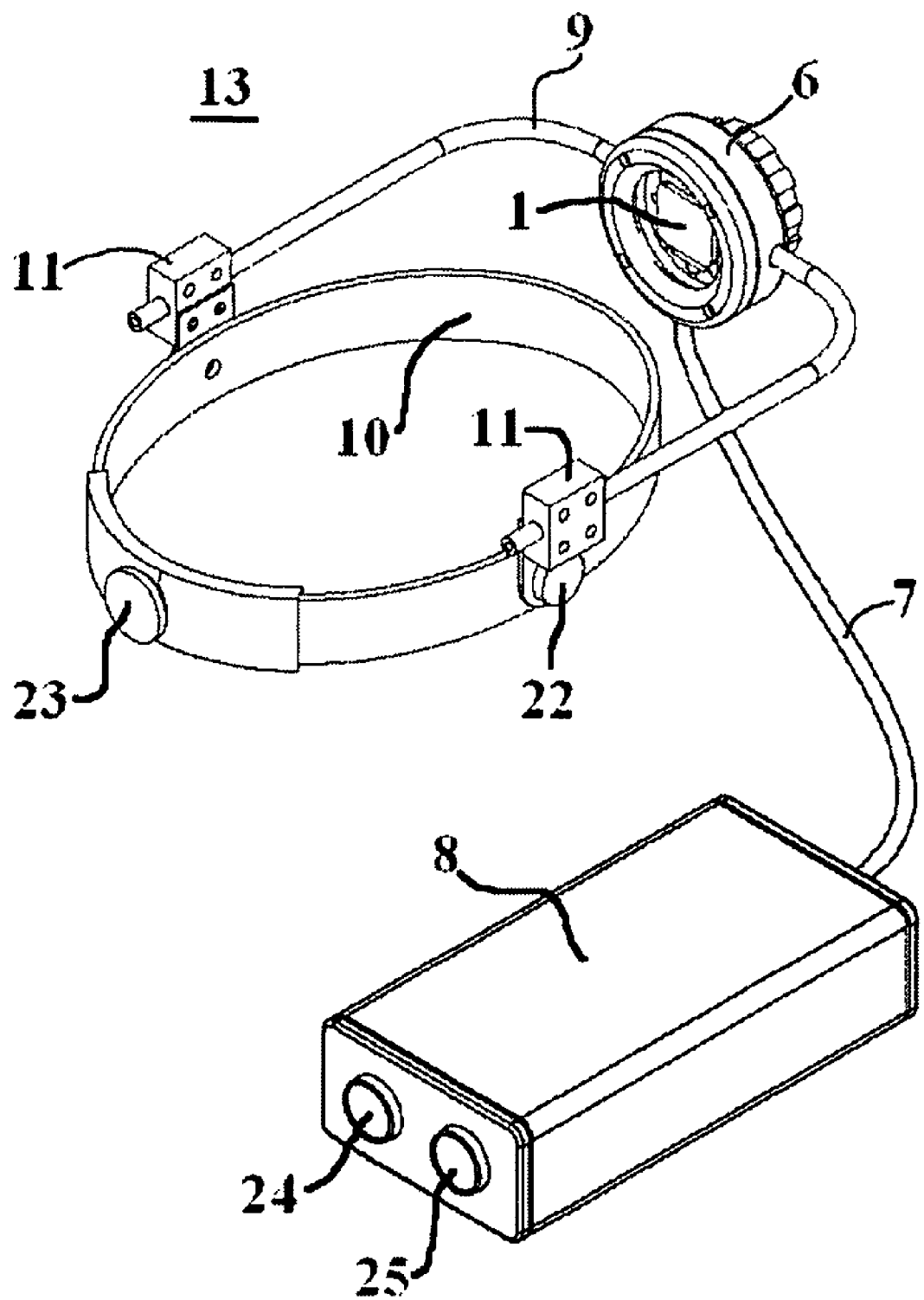
FIG. 1 presents the components of one embodiment of the present light device: the Parkinson's Light Device (13), without its external charger (12) and external computer (21).

Several drawings and illustrations have been presented to aid in understanding the present invention. The scope of the present invention is not limited to what is shown in the figures.

DETAILED DESCRIPTION OF THE INVENTION

All publications and patent applications cited herein are hereby incorporated by reference in their entirety to the same extent, as if each of them has been individually indicated to be incorporated by reference.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention and do not limit the scope of the invention.

The present invention is based on the discovery that living organisms (such as humans, animals and plants) benefit physiologically and/or psychologically from visible light modulated at particular frequencies, especially when such organisms are exposed to this light at certain intensities for certain durations of exposure. Benefits observed are a dramatic acceleration of healing, healing where a condition was not improving prior to exposure; and/or decrease in susceptibility to certain illnesses. For convenience, the present invention uses humans and patients to illustrate the invention. However, it is understood that the present invention is applicable to living organisms in general, and preferably humans. For convenience, the pronoun "he" or "she" may be used, but it is to be understood that the present invention applies to all sexes.

1. ADVANTAGES OF THE INVENTION

One of the primary advantages of the method is absence of any side effects, as the light used is normal visible light at intensities lower than bright daylight. Further, the present method and its devices are simple to use, inexpensive and portable, thereby providing greater distribution to those most in need of treatment. Further, the invention obviates the need of medication or invasive procedures, thus eliminating any side effects due to the foregoing.

2. LIGHT SEQUENCES

The light used in the present invention is also called the "therapeutic light".

The light is of a fixed intensity, but its output is modulated by turning it on and off electronically at a given frequency and with a given "duty cycle" (the ratio between the length of time on and the length of time off) thus changing the average intensity of the light.

One embodiment of the present invention presents a method for treating a living organism by exposing the living organism to a light having a desired modulation frequency and intensity ("duty cycle") for a period of time ("duration") suitable to improve or maintain its health or well being. The light may have one fixed frequency, intensity and duration; or the light may undergo one or more pre-specified sequences of frequencies, intensities, and durations ("light sequences"). When sequence(s) is/are used, the living organism may be exposed to one or more of the same or different sequences consecutively. Preferably, a patient is evaluated before and after the light treatment to ascertain whether any improvement or stabilizing effect is observed. The patient may be treated as often as needed, based on individual needs, and the sequence(s) may be repeated in one session, and/or the patient may be treated more frequently to increase the improvement or stabilizing effect. As the patient improves or his condition stabilizes, the frequency of treatment may be decreased. If the condition for which treatment is sought has been eliminated, the treatment may be terminated or maintained to prevent recurrence or to maintain general health or well being.

The following describes non-limiting examples of treatment regimens. For example, the light sequence can be repeated in one session of treatment. In one example, the patient may be exposed to two back-to-back light sequences of treatment in one sitting in one day. He may then return 2 or 3 days later, and be treated to yet another two back-to-back sequences of treatment in one sitting in one day. This treatment plan is followed, while the patient is evaluated before and after treatment, to assess his condition. The number of back-to-back sequences of treatment in one sitting, and the number of visits per period of time (e.g., in 2 to 3 days, in a week, a month, etc.) to the medical office, may be increased or decreased or terminated, respectively, depending on whether the patient's condition is improving, worsening, stabilizing, or resolved. For example, this treatment method may be applied to the light sequences of Examples 2 to 4. Since the light device is inexpensive and easy to use, and the controller can be pre-programmed with the needed light sequence(s) and to automatically turn off the light device when the necessary sequence(s) have been completed, the patient may buy or rent the light device and treat himself without visiting the medical office.

The term "to improve or maintain a living organism's health" or "therapeutic" includes to improve or maintain the physical, physiological, psychological or general well being of the living organism. It includes generally improving and maintaining the well being or health of an organism; alleviating his symptoms or his discomfort. Further, the human who uses the present light therapy can be suffering from a disease or he can be generally healthy but wishes to maintain or improve (or optimize) his general well being (physical or otherwise). In this application, for the sake of convenience, a human, a human patient, or a subject is used as an example of a living organism to illustrate the invention. However, it is understood that the living organism can be a plant or an animal; the animal can be a human or a pet animal.

Without wishing to be bound by the hypothesis, it is hypothesized that an organism is affected by exposure to a light at certain modulated frequencies. However, in the case where the organism is a human, the light used in the present invention ("therapeutic light") is pulsed at a frequency (repetition rate) that is not normally encountered by a human in his ordinary life. The light used in the present invention is typically a light that is pulsed at least about 1 kHz in frequency. Preferably, the light that is used has a repetition rate of from about 1 kHz to about 200 kHz.

Thus, one embodiment of the present invention presents a method for treating a living organism by exposing the living organism to a light that preferably has a repetition frequency from about 60 to about 95 kHz, an intensity from about 9,000 to about 15,000 Lux, and the time during which the organism is exposed to the light is from about 1 minute to 7 minutes. More preferably, the light has a repetition frequency from about 63 to about 93 kHz, an intensity from about 9,033.3 to about 14,520 Lux, and the time during which the organism is exposed to the light is from about 1 minute and 45 seconds to about 6 minutes and 15 seconds (See, the Tables in Examples 2 to 4, below, for the lowest and highest values for each parameter and factoring in their variations). Most preferably, the frequency is from about 64 to about 92 kHz, the intensity is from about 10,037 to about 13,200 Lux, and the time during which the organism is exposed to the light is from about 2 minutes to about 6 minutes (See, the Tables in Examples 2 to 4, below, for the lowest and highest values for each parameter).

Having described the light treatment method generally, as shown above, the following describes specific light sequences that may be used with the method.

2. EXAMPLES OF LIGHT THERAPY

The light therapy described herein may be applied in a darkened or a lighted environment. The therapeutic light may illuminate an area of any shape and size. For example, the illuminated area may be a circular area on the patient's body of about 2 to about 3 inches in diameter, and more preferably at least about 3 inch in diameter. The light may illuminate part of or the whole body of the organism such as a human.

Without wishing to be bound by the hypothesis, it is hypothesized that the therapeutic light may be shined onto ("illuminate") a part of or the whole body of the organism, with the exception of the eyes. Though the light can illuminate the part of or the vicinity of the body, which requires treatment (the "afflicted" part of the body, as discussed below), it is not necessary that this be the case. It is hypothesized that the therapeutic light may set up a resonance that reaches other parts of the body that is not exposed to the light. Thus, even if the light is shined onto the part of the body that is not afflicted, the afflicted part of the body that has not been illuminated may still benefit from the therapeutic light. Further, the therapeutic light does not have to reach the skin surface of the organism, the critical factor is the intensity of the light as it reaches the space surrounding the body. Obstructions such as clothing or hair have been found not to change the effectiveness of the light. The spacing of the light source from the body surface is only critical insofar as it affects the intensity of the light reaching the space immediately surrounding the body. (since the light does not have to reach the skin itself, it is hypothesized that the space surrounding the body contains some sort of energy field that is affected by the light. The intensity of the light at the 2-3 inch distance is correct for the current embodiment of the present invention)

For example, in the case of a human, the light can be shined onto the human's clothes, hair or skin—even though the distance of the light source from the body is critical (as stated above), the light does not necessarily have to reach the skin to achieve the beneficial effect observed. For instance, if the light is directed to the head of a human with a full head of hair, then the light can illuminate his hair and not necessarily reach the skin surface below with no decrease in the effectiveness.

Thus, as used in this application, the "intensity" of the light is measured at the area illuminated by the light. One embodiment of the invention is shown in Examples 1 to 4, the measurements in Examples 1 to 4 were taken directly at the centerline of the Lamina BL-3000 green LED array at a distance of 2.5 inches. (this corresponds to the 2-3 inch distance of this particular light source from the head)

The intensity of the light in the Examples 1 to 4 varies over the illuminated surface. It is more intense at the center than near the edge. (The actual distribution of the light intensity vs. angle with respect to the center line of the light source is illustrated in FIG. 5.)

The measurements listed in this document were taken directly at the centerline of the light-source at a distance of 2.5 inches. The intensity is listed in Lux. From the examples and discussion in this application, one skilled in the art would be able to determine the intensity on the illuminated area with regard to other light sources placed at varying distances from the illuminated area.

The following is a non-limiting example of a treatment method, using a human as an example of an organism: a part or the whole of the human (whether naked, in everyday clothing, or in hospital gown or sheet) is exposed to the treating light. For example, the part of the human body that is exposed to the light may be: (1) the part of the body that is diseased or unhealthy; (2) any part of the body or the energy field surrounding the body that has a relationship to the body function that is affected by illness, injury or any other non-optimum condition. (3) the injured parts of the body (such as a twisted ankle, strained muscles, etc.); (4) the part of the body for which the human desires to improve, e.g., in its well being, etc.; and (5) the whole body, e.g., if the human wishes to improve or maintain the health of his whole body; or just for convenience, e.g., many humans can sit in or walk through (be processed) the same room under a ceiling or pass walls on which is hung light sources (e.g., rows of lamps) emitting the desired light at one frequency and intensity, or one or multiple sequences of frequency and intensity. If the humans are sitting or walking beneath the light sources, then the time they spend in the room (or walk through the room) would determine their exposure time.

Light therapy may be used to treat various diseases and conditions, examples of which are found in the Examples section, below, which present the therapeutic sequences of light for treating the following diseases and conditions:

(2.1) Treating Parkinson's Disease: The light sequences useful for treating Parkinson's disease are found in Example 2, Table 1, and Example 4, Table 1a, below. With Parkinson's disease, the therapeutic light may be directed to the back of the head of the patient. According to the National Institute of Neurological Disorders and Strokes: Parkinson's disease is a progressive neurological disorder that results from degeneration of neurons in a region of the brain that controls movement. This degeneration creates a shortage of the brain signaling chemical (neurotransmitter) known as dopamine, causing the movement impairments that characterize the disease. It is believed that at this time there is no cure for this disease. Without wishing to be bound by the hypothesis, applicants hypothesize that the therapeutic light stimulates dopamine production, and thus, reduces or eliminates the symptoms of Parkinson's disease.

(2.2) Treating the Effects of Strokes which are caused by a blood clot: The light sequences useful for treating the effects of strokes are found in Example 3, Table 2, and Example 4, Table 2a, below. The light treatment alleviates or eliminates the after effects of stroke that were caused by a blood clot, e.g., the paralysis caused by stroke. The light may be directed to the location where the blood clot is located. For example, the light is shined onto the scalp or hair under which the blood clot is located.

(2.3) Treating Ataxia: The light sequences useful for treating some forms of ataxia are found in Example 4, Tables 3 and 3A, below. Ataxia describes a lack of coordination, which can be associated with infections, injuries, diseases, or degenerative changes in the central nervous system. The term ataxia also describes specific degenerative diseases of the nervous system called the hereditary and sporadic ataxia. Diagnosis of ataxia may include genetic testing and MRI brain scan. In the present invention, the light may be shined onto the head of the patient.

(2.4) Treating Diseases or Conditions of the Liver, Pancreas, Spleen, Kidney, Specific Organs and Tissues: The light sequences useful for specific organs and tissues are found in the Example 4, Tables 4 to 8 and table 4A, below. The therapeutic light may be shined onto the patient's skin over the area of the organ to be treated (such as his liver, pancreas, spleen, etc.), or the illuminated area covers an area that not only include the organ to be treated but its immediate surrounding. The light may even illuminate the patient's abdomen, thorax or torso where the organ or tissue to be treated is located. The light may be shined onto the front, the back, or both sides of the patient. Alternatively, if one or more small locations are to be illuminated, a portable light device or a light device that illuminates a small area may be used. For example, if a patient's knee suffers from torn ligaments, strained muscles, or broken bones (with broken blood vessels and pain), then the therapeutic light with the parameters specified for ligament, muscles, bones, blood vessels, and/or nerves, in Table 8, below, may be shined onto the knee and its surrounding to speed up recovery, to aid in healing, and to relieve pain.

In yet another embodiment, if a large area or many organs or tissues are to be treated, several devices may be used simultaneously, each set to provide the specific treating parameters for each organ or tissue, in accordance with the parameters of the Tables of Example 4. Alternatively, the patient may be in a room well illuminated by light(s), which changes according to the parameters of the Tables of Examples 2 to 4, to improve one or more of his organs or tissues or health in general.

3. LIGHT DEVICE

One embodiment of the present invention presents a light device, which is preferably portable. The portable light device comprises the following components:

(1) A light source. The light source may be contained in a surface illuminating unit. The surface illuminating unit may be an enclosure with a transparent window for the light to pass through. The surface illuminating unit may additionally contain a cooling fan for cooling the light source.

(2) A mount means for mounting said light source or surface illuminating unit adjacent to the living organism ("subject") to direct the light from the light source to a targeted area, which may be a part or the whole body of the subject, or the clothing etc., of the subject. Alternatively, the light sources may be incorporated into lighting fixtures for living and working spaces (taking the place of incandescent or fluorescent lights)—in this case the light frequencies and intensities scan through many different combinations so as to achieve the correct intensity at different distances from these light sources.

(3) A controller for controlling the light modulation frequency, intensity (by duty cycle), and the duration of the foregoing, (If a cooling fan is used, the controller preferably also controls the turning on and off of the fan.) The controller may be integrated with the light source and mount to form a self-contained unit, or it could be separate and connect to the light source with a removable cable. The controller would contain rechargeable batteries or operate from an external power supply.

(3.1) Light Source

The light source is capable of producing light at a specified modulation frequency and intensity for the required duration of time, e.g. as shown in one or more of the Tables of Examples 2 to 4, below. Examples of the light source are groups of LEDs or an LED array. Super bright light sources of very pure green light of about 525 nm peak wavelength may be used but other wavelengths may also prove effective.

In Example 1, the light source is Lamina BL-3000 green LED array. However, it is not necessary that the light source emits only green light, any other light may be used. For example, white light works. Other lights that may be used are blue and red lights. Similarly, other LED arrays and light sources may be used, so long as the light source can delivers light modulated at the stated frequencies, intensity, and duration required for a specific treatment. For example, if one wishes to apply Example 2 and its Table 2, below, he must use a light source that can emit the light having the properties listed in Table 2. If he wishes to use a light that can work for Examples 2 through 4, then he should use a light source that is capable of emitting the light within the ranges of the sequences found in the Tables of Examples 2 through 4.

(3.2) Mount Means

The mount means is for mounting said light source adjacent to the subject to deliver the light from the light source to the subject. The mount means may be made of any suitable materials, such as metal, plastic, etc. A headgear is an example of a suitable mount means if the light source is to be directed to a subject's head. An example of a headgear is shown in Example 1, below, and FIGS. 1 and 2. In other embodiments, the mount means can be a stand on which the light source is attached, and the subject is seated below the light source.

In Example 1, below, the light source is carried on an adjustable positioning mechanism attached to a mount means. However, other mount means may be used, and the adjustable positioning mechanism may not be necessary depending on the mount means. For example, although Example 1, below, discloses mounting the device on the human head by means of a headgear and the use of an adjustable positioning mechanism, the device may be supported by any other means and an adjustable positioning mechanism may be dispensed with. For example, the mount means can be a helmet or hood similar to the drying hood used in hair salon under which the patron sits. (the light source would be incorporated into the hood)

The mount means may be a chair, seat, etc., and one or more light sources are built into the mount means. For example, the light device comprising the chair or seat may be coin operated and be placed in public areas and the public may use them by inserting the coins and sitting on the chair or seat. The light device may also be non-portable. For example, the foregoing chair or seat may be portable or stationary and positioned fixedly onto a site. The mount means and light sources may resemble prior art track lights, or fluorescent lights, built into or mounted onto the ceiling or walls but modified by making or programming the light sources to emit light of the specified frequency and intensity, without change or with one or more different lights sequence(s), continuously or for a specified duration (which may be repeated at intervals, or may be a repeated sequence of light frequencies and intensities), to enhance the health or well being of occupants or passers by in the space so illuminated.

In order to position the light source in an optimum position for light treatment to the subject of different requirements, the mount means may include distance-adjuster for adjusting the distance between the light source and the subject, or an angle-adjuster for adjusting the angular relation between the light source and the targeted area of the subject. Alternatively, the adjustable positioning mechanism performs the function of distance adjuster and/or angle-adjuster. A typical distance for a head-mounted device is for the light source to be between around 2-4 inches from the subject's head, usually behind the head.

(3.3) Controller

The light device preferably includes a controller for controlling the light modulation frequency, intensity, and duration. In one embodiment of the invention, for example as disclosed in Example 1 below, the controller controls the light intensity by controlling the duty cycle of the light. As mentioned, the controller may be integrated with the light source and mount to form a self-contained unit, or it could be separate and connect to the light source with a removable cable. In the case of a non-portable application such as used in living or working environments the controller may be incorporated into the lighting fixture.

The controller may contain rechargeable batteries or operate from an external power supply. An external charger would be used to recharge the batteries from the mains.

The controller contains internal programming to execute the sequence of light modulation frequencies, duty cycles and durations. Preferably a start button initiates this sequence, which will then automatically progress until complete and a stop button on the controller allows the sequence to be stopped and the device to be turned off.

The controller may include a means to select the required sequence using additional buttons mounted on the controller.

The controller may be a self-contained unit with pre-programmed light sequence(s) and repetition(s) of the foregoing. Alternatively, to expand the possible number of light sequences and repetitions, the controller may be connected (e.g., via a computer interface RS232 or USB cable in the case of a laptop computer) to a computer that operates a computer program which enables the user to set the parameters for the modulation frequency, intensity (or duty cycle), and duration, for each step of a light sequence and, if need be, the repetitions of the sequence, and the time for starting and ending the sequence. In this way, the user can adjust the Light Device to a subject's particular conditions and/or requirements. The user can be a physician, a chiropractor, any health practitioner, or an informed member of the public, etc.

The computer program can exist in a variety of forms, both active and inactive. For example, the computer program and objects can exist as software comprised of program instructions or statements in source code, object code, executable code or other formats; firmware program(s); or hardware description language (HDL) files. Any of the foregoing can be embodied on a computer readable medium, which include storage devices and signals, in compressed or uncompressed form. Exemplary computer readable storage devices include conventional computer system RAM (random access memory), ROM (read only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the computer program can be configured to access, including signals downloaded through the Internet or other networks. Concrete examples of the foregoing include distribution of executable software program(s) of the computer program on a CD ROM or via Internet download. In a sense, the Internet itself, as an abstract entity, is a computer readable medium.

Thus, some aspects of the present invention include: a controller pre-programmed with one or more of the light sequences and/or repetition(s) thereof; a computer program for executing one or more of the light sequences and/or repetition(s) thereof, and the computer containing the computer program; a computer capable of executing one or more of the light sequences and/or repetition(s) thereof, or allowing the user to change the parameters of the light sequences; a light device having the foregoing controller or recoverably connected to the foregoing computer, wherein said light device has a light source that can step through one or more of the light sequences and/or repetition(s) thereof. The preferred light sequences are those set forth in the Tables of Examples 2 to 4.

Given the disclosure in this patent application and what is known in the art, one skilled in the art would be able to construct various embodiments of the light device (including its optional components) and its electronics, and to create the computer and controller programs to enable the functioning of the various embodiments of the light device (including its optional set-ups) and to execute the functions described in Examples 1 to 5.

The above and other advantageous features of the present invention will become more apparent from the following description of the embodiments when taken in conjunction with the attached drawings.

EXAMPLES

Example 1

The Parkinson's Light Device

Figure 2:
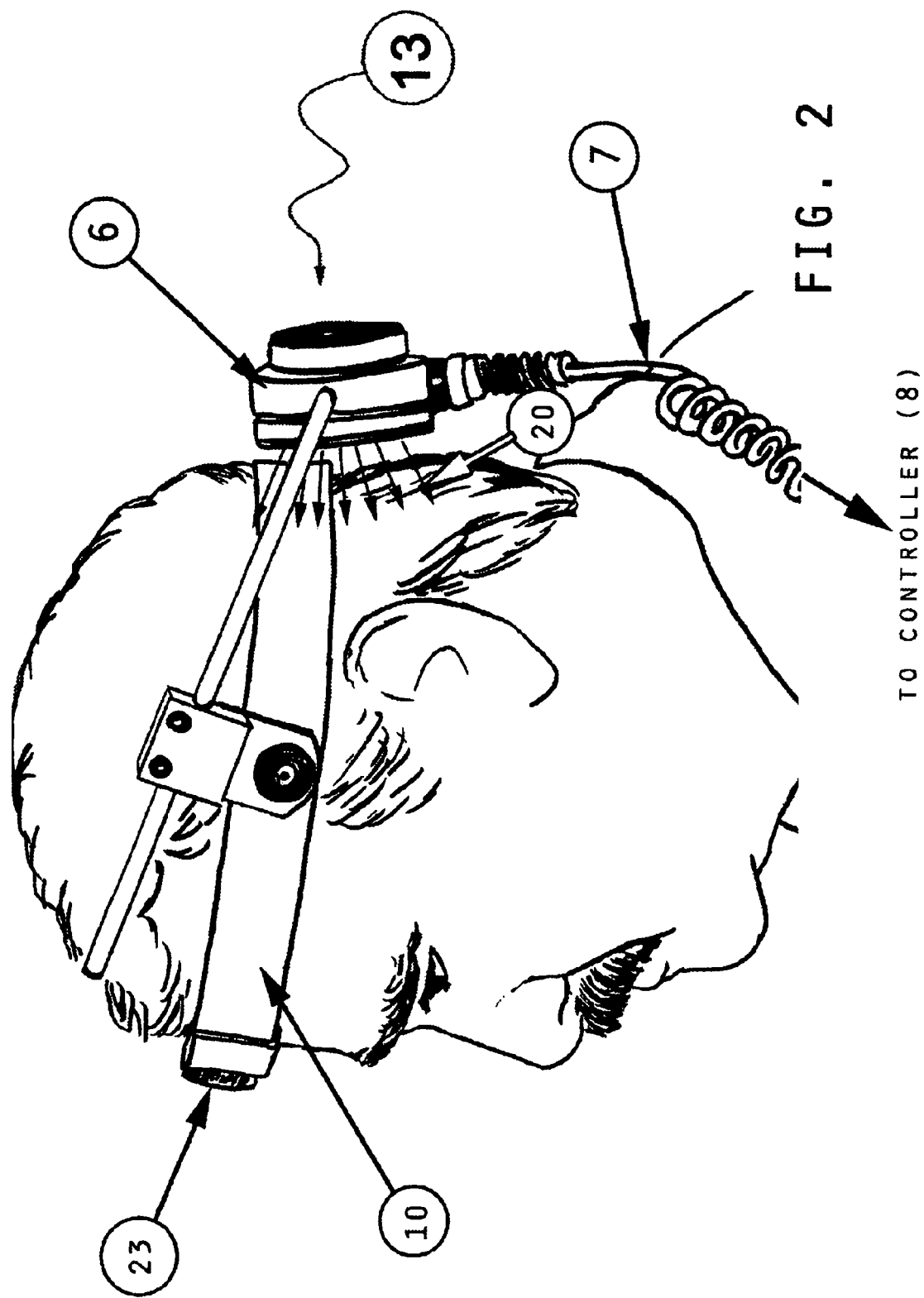
FIG. 2 presents the side view of one embodiment of the present light device and its use: the Parkinson's Light Device (13) placed on the person's head with the light illuminating the back of the head.

This Example presents a non-limiting example of a portable light device of the present invention and the electronic system for operating it. In this Example, the portable light device is called the Parkinson's Light Device (13), and its components are shown in FIGS. 1 and 2. In FIG. 2, the Parkinson's Light Device (13) is shown as used on a patient for treating Parkinson's disease (Examples 2 and 3, below). As shown in FIGS. 1 and 2, the Parkinson's Light Device (13) consists of the following:

1) A headgear (10)—which allows the device to be strapped to the head of the patient. In the Parkinson's Light Device (13), the headgear (10) is adjustable, so that it can be adjusted to fit the patient's head. The head gear may be adjusted for the size of the patient's head using means known in the art, such as by means of a belt and buckle set-up. In the Parkinson's Light Device (13), the headgear is adjusted by means of turning the knob on the headgear. The headgear (10) can be made of any suitable material, such as plastic, leather, metal, or rubber, etc. In Parkinson's Light Device, the headgear (10) is made of plastic.

2) An adjustable positioning mechanism—which allows the light source to be positioned at a correct distance over the area to be illuminated. In the Parkinson's Light Device (13), the adjustable positioning mechanism consists of a U-shaped rod (9). At the bottom of the "U" of the U-shaped rod (9), is attached a surface illuminating unit (6) containing the light source (the LED array (1), described below) and cooling fan (4). Each opposing leg of the U-shaped rod (9) is attached to the head gear by an adjustable attachment means (11) that are attached onto each opposing side of the headgear (10) and that allows the opposing arms of the U-shaped rod (9) to move (pivot) relative to the head gear (10), thus allowing the adjustment of the angle and height at which the light source (the LED array (1), described below) is to be placed relative to the head of the subject. Any attachment methods or means may be used to attach each opposing arm of the U-shaped rod (9) to the adjustable attachment means (11), which in turn is attached onto each opposing side of the headgear (10). The U-shaped rod (9) and the adjustable attachments means (11) can be made of any suitable material, such as plastic, metal, etc. In the Parkinson's Light Device (13), the U-shaped rod (9) and the adjustable attachments means (11) are made of metal. The detailed discussion is provided further below.

3) A light source—in the Parkinson's Light Device (13), a high intensity LED array (1) serves as the light source, and a cooling fan (4) is provided to cool the LED array (1) which tends to heat up. For convenience and the protection of the light source and fan, both are contained in a surface illuminating unit (6).

4) A self-contained controller with a power source. In the Parkinson's Light Device (13), the light source (LED array 1) and cooling fan (4) are connected to a controller (8), which controls the functioning of the light source and cooling fan. Controller (8) is self-contained and portable, and it contains rechargeable batteries. For the convenience of the user of the Parkinson's Light Device (13), an independent battery charging unit (in the form of an external charger 12) is provided for charging the battery (14), as needed (see FIG. 3).

In FIG. 2, the light source is shown to be mounted on the back of the patient's head in order to shine onto the back of the head (as discussed in Example 2, below). It is envisioned that for other applications, the light source may be mounted so as to shine onto other locations of the head or body, the whole body, or part or all the covering (e.g., clothing, hospital sheet and gown) on the body, at various distances, and covering various areas of illumination. For example, larger or smaller light sources may be used to vary the areas of illumination.

The device is explained in detail below:

As shown in FIGS. 1 and 2, the device comprises a surface illuminating unit (6) which is attached to a U-shaped rod (9) which in turn is attached to a head gear (10). The head gear (10) serves as a mount member by which the surface illuminating unit (6) is worn on the head of a subject to locate the surface illuminating unit (6) at the back of the subject's head (as shown on FIG. 2). The surface illuminating unit (6) has a light source, which illuminates a substantially circular area on the subject's scalp (as shown on FIG. 2). In the Parkinson's Light Device (13), the light source can be a Lamina BL-3000 green LED array (Part # BL-32C1-0144 or similar unit, commercially available from Lamina Ceramics, Westampton, N.J., USA). The Lamina BL-3000 green LED array is configured with 39 cavities, each populated with multiple LEDs. The Lamina BL-3000 green LED array is selected for its high brightness, high luminous intensity in very small footprints, and its long LED life and good reliability.

The typical beam pattern of the Lamina BL-3000 green LED array is shown in FIG. 5. FIG. 5 is the black-and-white version of the graph found on page 3 of the Lamina Ceramics's brochure: *Brilliant Light! BL*-3000 Series, Part # BL-32C1-0144, revised 01.20.05. The foregoing Lamina Ceramic's brochure, page 2, also presents the following Table A of technical data, of which the wavelength of the light is relevant to the present application, and the wavelength (lambda) is typically 525 degree K. The LED array is a super bright light source of very pure green light of about 525 nm), and its frequency (repetition rate) and intensity can be controlled by a duty cycle of about 10% to about 90%

TABLE A

Technical Data of Part # BL-32C1-0144

| | Symbol | Min | Typical | Max | Unit |
|---|---|---|---|---|---|
| Wavelength | λ | 515 | 525 | 535 | Nm |
| Forward voltage* | Vf | | 10.7 | | V |
| Test Current | If | | 2.3 | | A |
| Power* | P | | 24.6 | | W |
| Luminous Flux* | φ | | 570 | | Lm |
| Thermal Resistance | Tr | | 0.66 | 0.88 | deg C./W |

*note 1: Optical and Electrical specifications are given for the specified drive current at a 25 deg C. temperature.

In the Parkinson's Light Device (13), a cooling fan (4) is used to cool the LED array (1). As instructed by Lamina Ceramics, the cooling fan (4) has a cooling capacity to keep the LED die junction to below 125° C. For more details on the LED array and cooling requirement, see Lamina Ceramics's brochure: Brilliant Light! BL-3000 Series, Part # BL-32C1-0144, revised 01.20.05.

As shown in FIG. 4A to 4C, The present device contains a surface illuminating unit 6 (in which the LED array is housed) that ensures that the emitted light 20 (see FIG. 1) is dispersed onto a substantially circular surface on the target having an effective illuminated area of approximately 3 inches diameter (when the LED array is placed at a distance of about 2 to about 3 inches from the illuminated area or target 19) and radiates the light in a 6-step sequence, as shown in Table 1 of Example 2.

As shown in FIG. 4A to 4C, the surface illuminating unit comprises a metal casing (3) accommodating LED array (1) serving as the light source which shines through a transparent window (5) held in place by a metal or plastic ring (2). The metal housing conducts the heat from the LED array to the back, where it is dissipated by the cooling fan (4).

Figure 3:
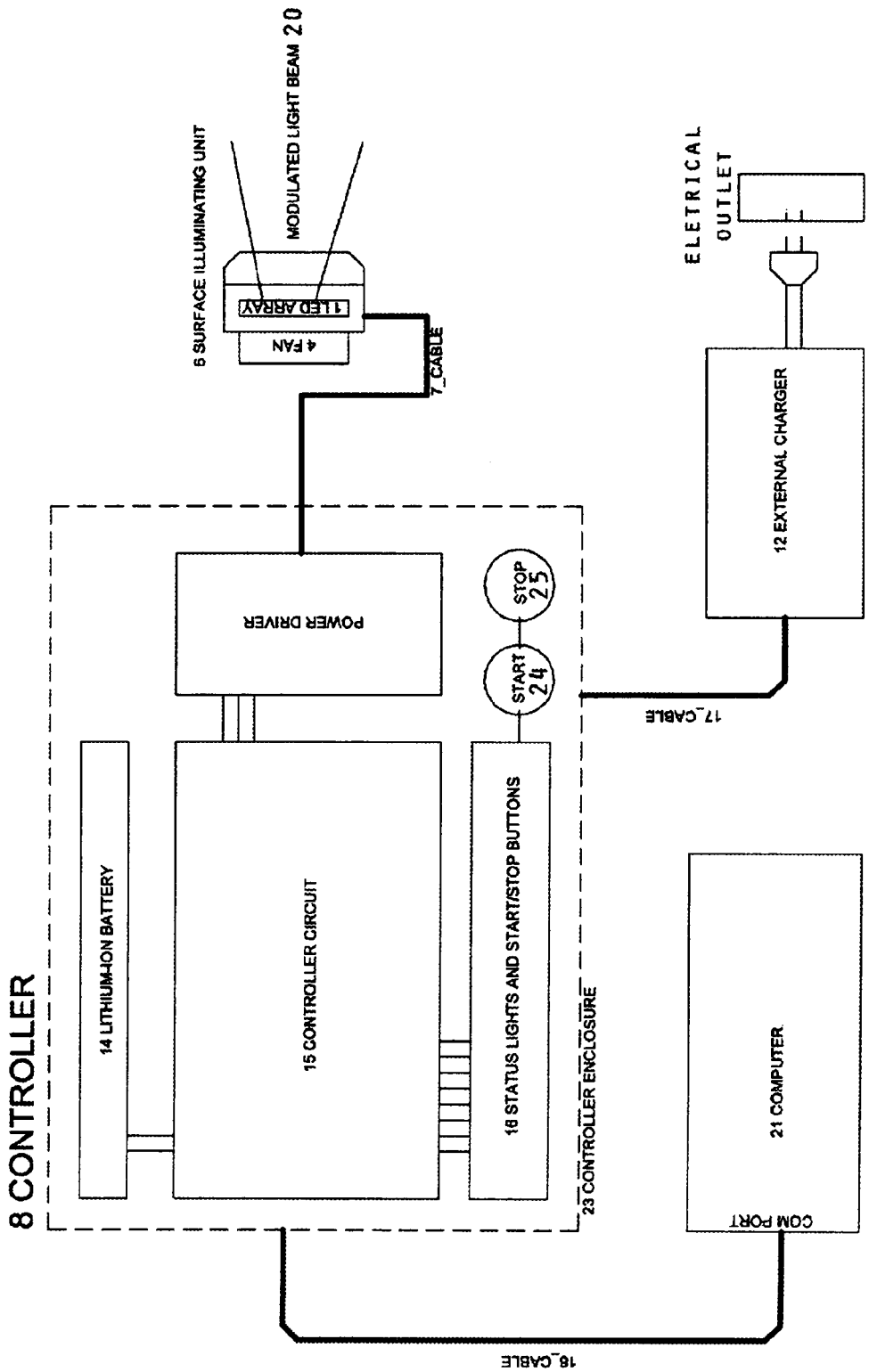
FIG. 3 is one embodiment of the block circuit diagram of a controller: the controller (8) of the Parkinson's Light Device (13). Also shown are the connection to the external charger (12) and the external computer (21).

The LED array (1) and cooling fan (4) are connected through a cable (7) to controller (8) which accommodates a lithium battery (14) which powers the LED array (1), the cooling fan (4), and the controller circuit (15) (see FIG. 3). The battery can be any suitable battery known in the art. In Examples 2+3 it is a lithium battery.

As shown in FIG. 3, the controller circuit (15) is programmed with (or is stored with) the parameters for the light sequences. Thus, the controller circuit (15) controls the LED array (1) and enables it to execute the specified light sequences and/or their repetitions, such as those shown in the Tables of Examples 2 to 4, below. In FIG. 3, the controller (8) also incorporates the driver electronics for the LED array.

The controller (8) also features a "Start" button (24) that begins the sequence when pressed and a "Stop" button (25) to turn the unit off manually. A status light (16) shows that the unit is running properly and warns the user if the battery (14) goes too low. An audible indicator alerts the user when the sequence has completed.

In Examples 2 and 3, below, a controller (8) that was self-contained and pre-programmed with the light sequences of Examples 2 and 3, respectively, was used as shown in FIGS. 1 and 2. Unlike FIG. 3, the Parkinson's Light Device (13) of Examples 2 and 3 was not connected to a computer (21). The Parkinson's Light Device (13) of Examples 2 and 3 was limited to the number of light sequences that can be pre-programmed into the controller. Generally, each controller is programmed with one light sequence only, but capability of the Parkinson Light Device (13) may be expanded, by using an optional external computer (described further below).

In Examples 2 and 3, below, the controller circuit (15) sets the modulation frequency, duty cycle (that determined the intensity), and duration of the light for the light sequences of Examples, 1 and 2, respectively. When changing from one step to the next step of the light sequence, the frequency and duty cycle are changed.

When the Parkinson's Light Device (13) is turned on, it will automatically execute the pre-programmed (into the controller) sequence of light frequencies (repetition rates), duty cycles (pulse widths that determine intensities), and durations. Examples of a sequence are those shown in the Tables of Examples 2 to 4, for the relevant diseases or conditions. Generally, one sequence is pre-programmed into the controller (8). Once a sequence is complete, the Parkinson Light Device (13) will sound an audible signal and switch itself off. The Parkinson's Light Device's internal battery (14) is a lithium battery capable of storing sufficient energy for completing two light sequences. One skilled in the art would realize that he could replace battery (14) with other types of batteries or a longer lasting battery to provide more energy to complete more light sequences. An optional external charger (12), for recharging the battery (14), is an external and independent unit that can be removeably and electronically connected to the controller (8) by cable (17). as shown in FIG. 3. As with conventional charger for portable electronic equipments, the external charger (12) can in turn be plugged into an electric outlet.

For its protection, the controller (8) is encased in an extruded aluminum housing (23). One skilled in the art would realize that the housing could be made of any suitably protective material. As shown in FIGS. 1, 2 and 3, the controller can be provided separately from the surface illuminating unit (6), so as to be separately portable.

As shown in FIGS. 1 and 2, the surface illuminating unit (6) is attached to the U-shaped rod (9)—the surface illuminating unit (6) being attached to the bottom of the "U". The U-shaped rod (9) is made of metal. Each opposing arms of the U-shaped rod (9) is passed through a adjustable attachment means (11) with its lower end being an adjustable hinge (22) The arrangement enables the U-shaped rod (9) to be adjusted (by articulating around the hinge (22) and sliding in or out of the attachment means 11) in an angle relative to the headgear (10), so that the LED array (1) (in the surface illuminating unit (6) can be positioned over the subject's head at an appropriate angle and distance. One skilled in the would realize that the U-shaped rod (9), the head gear (10), the adjustable attachment means (11) can be made of any suitably sturdy material; and that the hinge (22) can be any type of joint known in the art (other than a hinged joint) that enables the user to adjust the angle and distance of the LED array (1) over the area to be illuminated. In this Example 1, the attachment means is made of aluminum and plastic.

Distance from the Illuminated Target and the Light Intensity at the Illuminated Area—When using the Parkinson's Light Device (13), the LED array (1) is typically located about 2 to 3 inches from the target (area to be illuminated) on the patient's body. The illuminated area was about circular in shape and of about 3 inches in diameter. To measure the intensity of the light, a light meter, with the name of GOSSEN, model LUNAPRO (however, any light meter may be used) was set up at 2.5 inches from the LED array (1) of the Parkinson Light Device (13). The 2.5 inches distance was chosen by taking into account that the LED array (1) is typically located about 2 to 3 inches from the target (area to be illuminated). The intensity of the light was measured at the center of the illuminated area. Aimed at the centerline of the LED array with the diffuser set in place. The frequency was not measured, as we only need to know the intensity. Since the Parkinson's Light Device (13) controls the light (emitted by the LED array 1) by changing the duty cycle (and thus the intensity) and modulation frequency of the light energy, applicants could establish the relationship between the duty cycle and the light intensity. The light intensity is herein measured using the Lux unit. Lux is a measurement of units of illuminance. That is:

1 Lux=1 lumen per square meter.
100% Duty cycle=13,750 Lux

For example, 50% Duty cycle=0.5×13,750 Lux=6,875 Lux

Another example, 80% Duty cycle=0.8×13,750 Lux=11,000 Lux

The measurement method used herein has an accuracy of ±10%. In the tables of the following Examples 2 to 4, the light intensity measured according to the above method is shown, and the actual light intensity value might vary within the range of plus-or-minus 10% of the stated value. Since this light intensity was measured at the center of the illuminated area, this light intensity is applicable to any light source, light device, and the distance of the light source from the illuminated area, and the illuminated area. On the other hand, the tables also show the duty cycles that would generate such light intensity, when using the LED array 1 of the Parkinson's Light Device in which the LED array 1's typical location is about 2 to about 3 inches from the illuminated area, and the illuminated area is about 3 inches in diameter.

Optional Expansion of the Parkinson's Light Device Using Computer: As discussed above, the self-contained controller 8 is constrained by the number of light sequences that can be programmed into it. The Parkinson Light Devices (13) may be expanded (as shown in FIG. 3) by recoverably or permanently connecting it to a computer (21). Preferably, the computer (21) is an external and independent unit that can be recoverably and electronically connected to the controller (8), such as by an optional external computer interface cable (18), as shown in FIG. 3. These optional parts are further described below.

The computer (21) may be any form of computer, non-limiting examples of which are a personal computer, a laptop computer, a PDA ("Personal Digital Assistant") such as a Palm or pocket PC handheld device. The optional external computer interface cable (18) may be provided to allow the controller (8) (whether or not pre-programmed with a light sequence) of a light source (1) to be connected to a computer containing a computer program for setting the parameters for the sequence, frequency, duty cycle (or intensity), and duration of different light sequences, and/or the number of repetitions for each light sequence. Using the computer keyboard, the user can then pick and choose the parameters applicable to the particular need of a subject. For example, the user can enter the values for each step of the sequences, as given in the tables of Examples 2 to 4, below, for the respective disease or condition. The expanded range of different light sequences enables the light device (such as the Parkinson's Light Device (13) to be used for different treatments, according to the specific condition of the subject. The Parkinson's Light Device (13) uses RS232 (cable 18) to enable computer (21) to communicate with controller (8). However, the communication may be effectuated with any device, other than RS232, known in the art.

In one example, the Parkinson's Light Device (13) may be controlled by the controller (8) (such as a controller pre-programmed with the 6-step light sequence for treating Parkinson's disease of Example 2), but the optional computer interface cable (18) is provided if the user wishes to use other light sequence(s) not pre-programmed into the controller (8), but that may be separately provided by a software installed (or can be installed) into the computer (21).

Preferably, the computer (21) has a display screen that allows the user to see and select (set up) the different parameters of the light. In one embodiment, the adjustable light frequencies, duty cycle (or intensity) and duration are used. The settings may be saved in a file on the computer. The computer can be set up to scan through a series of different frequencies and intensities, one after another (e.g., scanning through the series of frequencies, intensities, and durations shown in Example 4, Table 8, below). The duration of each setting can be set up.

Given the disclosure in this patent application and what is known in the art, one skilled in the art would be able to construct the Parkinson's Light Device (including its optional components) and its electronics, and to create the computer and controller programs to enable the functioning of the Parkinson's Light Device (including its optional set-ups) and to execute the functions described in Examples 1 to 5.

Example 2

Light sequence for Parkinson's Disease

Applicants found that light modulated at certain frequencies, intensities and durations has a beneficial effect in patients suffering from Parkinson's disease.

In the patient treatment of this Example 2, the Parkinson's Light Device (13) of Example 1 was used on the patients as shown in FIG. 2, and as described in Example 1 but without using the optional computer (21) and external charger (12). With the aid of the controller (8), the Parkinson's Light Device (13) scanned through a series of frequencies, duty cycles (resulting in the corresponding intensities, as shown in Table 1, below) to illuminate the patients. The LED array 1 was positioned according to FIG. 2, at about 2 to about 3 inches from behind the patient's head, the light beam (20) was directed to the back of his head. As shown in FIG. 2, the area illuminated by the light was a near circular shape of about 3 inches in diameter on the patient's scalp covering the back of his head. In Table 1, below, the duty cycle is specific to the Parkinson's Light Device (13) used as described herein.

The intensity corresponding to each duty cycle was measured according to the method described in Example 1, under the section "Distance from the Illuminated Area and the Light Intensity at the Illuminated Area", above. The intensity is applicable to any light source or light device, distance from the illuminated area, and the size and shape of the illuminated area, including the Parkinson's Light Device (13) and its use discussed herein. Table 1 presents the 6-step light sequence used with the Parkinson's Light Device (13) for treating Parkinson's disease. In the Tables of Examples 2 to 4 and their discussion, the term "time" is synonymous with duration.

TABLE 1

6-Step Light sequence for Parkinson's Patients
Using the Parkinson's Light Device

| Step | Frequency (kHz) | Duty cycle (%) and its corresponding light intensity (Lux) | Time (minutes) |
|---|---|---|---|
| 1 | 78.0 | 90% = 12,375 Lux | 4 |
| 2 | 78.6 | 86% = 11,825 Lux | 2 |
| 3 | 74.0 | 78% = 10,725 Lux | 3 |
| 4 | 72.0 | 77% = 10,587 Lux | 3 |

TABLE 1-continued

6-Step Light sequence for Parkinson's Patients
Using the Parkinson's Light Device

| Step | Frequency (kHz) | Duty cycle (%) and its corresponding light intensity (Lux) | Time (minutes) |
|---|---|---|---|
| 5 | 68.0 | 84% = 11,550 Lux | 3 |
| 6 | 64.0 | 86% = 11,825 Lux | 2 |

Table 1 shows that the light treatment was applied in a six-step sequence. For example, in Step 1, the light's frequency was 78 kHz with a duty cycle of 90% that produced an intensity of 12,375 Lux, and the foregoing light frequency and duty cycle (and its corresponding intensity) were applied for 4 minutes, before proceeding to Step 2, wherein the light frequency of 78.6 kHz and a duty cycle of 86% (producing a corresponding 11,825 Lux of intensity) were applied for 2 minutes, and so on, until Step 6 was completed.

Nine patients, males and females of various ages were treated with the Parkinson's Light Device 13. They have been suffering from the disease for 4 to 20 years, and all were on Parkinson's medications. They did not stop with their medication when undergoing the light therapy of the present invention. When they presented themselves at the test site, they suffered from uncontrollable tremors at rest, drooling, slurred and barely audible speech, and the typical gait and facies commonly associated with Parkinson's disease. The therapeutic light was shone onto the back of the patient's head (as described above) and according to the light sequence of Table 1. Each reported immediate improvement at the end of the treatment, and their symptoms have disappeared. All were treated only once with two times the light sequence of Table 1 (i.e., repeating the sequence once), and there was no follow-up.

Example 3

Light Sequence for Stroke Patients

TABLE 2

5-Step Light Sequence for Stroke Patients
using the Parkinson's Light Device

| Step | Frequency (kHz) | Duty cycle (%) Intensity (Lux) | Time (minutes) |
|---|---|---|---|
| 1 | 78.6 | 74% = 10,175 Lux | 4 |
| 2 | 75.0 | 76% = 10,450 Lux | 6 |
| 3 | 85.0 | 88% = 12,100 Lux | 3 |
| 4 | 78.0 | 84% = 11,550 Lux | 3 |
| 5 | 73.0 | 76% = 10,450 Lux | 2 |

This Example 3 used the Parkinson's Light Device (13) and treatment method of Example 2, except that the above 5-step light sequence of Table 2 was used instead of the 6-step light sequence of Table 1 of Example 2.

Two patients who suffered from strokes as a result of blood clots were treated. They had blood clots that originated in the extremities and traveled to their brains, leading to partial paralysis. Patient #1, a 53 year-old male, cut his right knee with a box knife. While driving to work on the freeway he suffered a stroke and crashed his car. He was released from the hospital three weeks later, barely able to move his left leg or left arm, unable to move his fingers, and he lost the vision in his left eye. His fingers were locked in a claw-like position. He was treated four times, over a two-week period. At the end of the first session of the five-step sequence he was able to move all his fingers and touch the tip of his left thumb with the tip of the left little finger, and he was able to raise his left arm. At the end of the second session he regained most of the strength in his left arm, and some of the strength of his left leg, and his gait was almost normal. His left hand and fingers were moving as they had before the stroke. By the end of the third session he regained his full strength and walked without a limp. By the end of the fourth session the sight returned to his left eye. He stated that he felt no residuals from the stroke. The second patient was a 49 year-old female, who was accompanied by her doctor, who heard about the success of the first patient and wanted her to try the device. She was unable to walk, and had limited use of her arms and hands. She was treated twice, four days apart each time with one 5-step light sequence. At the end of the first session she regained full use of her arms and hands, and was able to move her legs and toes slightly. At the end of the second session she was able to stand up unassisted and take some steps.

Example 4

Other Light Sequences and Acceptable Ranges

Applicants also determined that the following tabulated sequences of light would benefit the conditions stated. The three key parameters for defining the light are: frequency, intensity and duration, and they are applicable to any light source. These parameters are shown in the tables. The tables are to be interpreted by keeping in mind Examples 1 to 3, above. That is, in the tables of Examples 2 to 4, the duty cycle is specific to the LED array 1 and the Parkinson's Light Device (13) used as described in Example 1, including the distance from the illuminated area. Thus, the Parkinson Light Device (13) as used in Example 1 is the preferred device to be used with the duty cycles for the Tables, though it may illuminate a different part of the patient's body, his clothing or sheet covering him, instead of his head. Instead of duty cycle, the corresponding intensity listed in the tables may be used to control the light source or determine the light's characteristic, in which case, the light source, device, distance of the illuminated area may be varied, so long as the intensity at the illuminated area meets the criteria of the tables. The intensity may be measured according to the method of Example 1, or by any method acceptable in the art. Thus, the light intensity, frequency and duration disclosed in the tables are generally applicable to any light source and light device, and to the distance of the light source from the illuminated area, and is not limited to only the Parkinson's Light Device (13) used as described in Example 1.

The tables of Examples 2 to 3, above, disclose the most preferred light sequences in their Tables 1 and 2, respectively. The following Tables 1a and 2a, present the preferred ranges of each parameter in the light sequence of Tables 1 and 2, respectively, by taking into account the plus-or-minus (±) variations (margins of error). Similarly, in tables 3 to 8 below, the most preferred light sequence for each table is the sequence with the stated parameters without taking into account the plus-or-minus variations. The plus-or-minus variations provide the preferred ranges of the stated parameters. For example, the most preferred sequence for Tables 3 and 4 would be the following Tables 3a and 4a, respectively. Tables 5 to 8 are to be interpreted in the same manner.

TABLE 3a

Light sequence for Ataxia Patients

| Step | Frequency (kHz) | Duty cycle (%) | Intensity (Lux) | Time (minutes) |
|---|---|---|---|---|
| 1 | 76.0 | 84 | 11,550 | 4 |
| 2 | 74.0 | 82 | 11,275 | 2 |
| 3 | 64.0 | 76 | 10,450 | 3 |

TABLE 4a

Light sequence for Liver Patients

| Step | Frequency (kHz) | Duty cycle (%) | Intensity (Lux) | Time (minutes) |
|---|---|---|---|---|
| 1 | 73.0 | 80 | 11,000 | 3 |
| 2 | 76.0 | 73 | 10,037 | 2 |
| 3 | 87.8 | 90 | 12,375 | 3 |
| 4 | 82.0 | 74 | 10,175 | 3 |

Thus, in the following Tables, the listed values are the most preferred values. The preferred (plus-or-minus) variations are also shown. The variations are interpreted as follows: the frequency can be varied within a range of plus-or-minus 1 kHz of the listed value. Similarly, the duty cycle can be varied within a range of plus-or-minus 5%, the intensity can be varied within a range of plus-or-minus 10%, and the time can be varied within a range of plus-or-minus 15 seconds of the listed values. For example, for Table 1a, Step 1, the frequency, duty cycle, intensity and time, are in the ranges from 77 kHz to 79 kHz, 85% to 95%, 11,137.5 Lux to 13,612.5 Lux, and 3 minute 45 second to 4 minute 15 seconds, respectively; the preferred frequency, duty cycle, intensity and time, are 78 kHz, 90%, 12,375 Lux, and 4 minutes, respectively.

Non-limiting examples of the applications of these tables of sequences may be found in the above Section 2, "2. Examples of Light Therapy" in general, and its sub-sections (2.1) to (2.4) in particular for the particular diseases and conditions listed in the Tables below.

TABLE 1a

6-Step Light sequence for Parkinson's Patients

| Step | Frequency (kHz) ± 1 kHz | Duty cycle (%) ± 5% | Intensity (Lux) ± 10% Lux | Time (minutes) ± 15 seconds |
|---|---|---|---|---|
| 1 | 78.0 | 90% | 12,375 | 4 |
| 2 | 78.6 | 86% | 11,825 | 2 |
| 3 | 74.0 | 78% | 10,725 | 3 |
| 4 | 72.0 | 77% | 10,587 | 3 |
| 5 | 68.0 | 84% | 11,550 | 3 |
| 6 | 64.0 | 86% | 11,825 | 2 |

TABLE 2a

5-Step Light Sequence for Stroke Patients

| Step | Frequency (kHz) ± 1 kHz | Duty cycle (%) ± 5% | Intensity (Lux) ± 10% | Time (minutes) ± 15 seconds |
|---|---|---|---|---|
| 1 | 78.6 | 74 | 10,175 | 4 |
| 2 | 75.0 | 76 | 10,450 | 6 |
| 3 | 85.0 | 88 | 12,100 | 3 |
| 4 | 78.0 | 84 | 11,550 | 3 |
| 5 | 73.0 | 76 | 10,450 | 2 |

TABLE 3

Light sequence for Ataxia Patients

| Step | Frequency (kHz) ± 1 kHz | Duty cycle (%) ± 5% | Intensity (Lux) ± 10% Lux | Time (minutes) ± 15 seconds |
|---|---|---|---|---|
| 1 | 76.0 | 84 | 11,550 | 4 |
| 2 | 74.0 | 82 | 11,275 | 2 |
| 3 | 64.0 | 76 | 10,450 | 3 |

TABLE 4

Light sequence for Liver Patients

| Step | Frequency (kHz) ± 1 kHz | Duty cycle (%) ± 5% | Intensity (Lux) ± 10% Lux | Time (minutes) ± 15 seconds |
|---|---|---|---|---|
| 1 | 73.0 | 80 | 11,000 | 3 |
| 2 | 76.0 | 73 | 10,037 | 2 |
| 3 | 87.8 | 90 | 12,375 | 3 |
| 4 | 82.0 | 74 | 10,175 | 3 |

TABLE 5

Light sequence for Pancreatic Patients

| Step | Frequency (kHz) ± 1 kHz | Duty cycle (%) ± 5% | Intensity (Lux) ± 10% Lux | Time (minutes) ± 15 seconds |
|---|---|---|---|---|
| 1 | 68.0 | 90 | 12,375 | 3 |
| 2 | 73.0 | 74 | 10,175 | 4 |

TABLE 6

Light sequence for Spleen Patients

| Step | Frequency (kHz) ± 1 kHz | Duty cycle (%) ± 5% | Intensity (Lux) ± 10% Lux | Time (minutes) ± 15 seconds |
|---|---|---|---|---|
| 1 | 84.0 | 86 | 11,825 | 2 |
| 2 | 76.0 | 76 | 10,450 | 3 |
| 3 | 86.0 | 80 | 11,000 | 2 |
| 4 | 89.0 | 83 | 11,412 | 3 |

TABLE 7

Light sequence for Kidney Patients

| Step | Frequency (kHz) ± 1 kHz | Duty cycle (%) ± 5% | Intensity (Lux) ± 10% Lux | Time (minutes) ± 15 seconds |
|---|---|---|---|---|
| 1 | 75.0 | 80 | 11,000 | 3 |
| 2 | 79.0 | 78 | 10,725 | 2 |

TABLE 8

Light Treatment for Specific Organs and Tissues

| Listed items | Patient's Organs or Tissue to be Treated | Frequency (kHz) ± 1 kHz | Duty cycle (%) ± 5% | Intensity (Lux) ± 10% Lux | Time (minutes) ± 15 seconds |
|---|---|---|---|---|---|
| 1 | Bladder (urinary) | 92 | 96 | 13,200 | 4 |
| 2 | Blood vessels | 75 | 90 | 12,375 | 2 |

TABLE 8-continued

Light Treatment for Specific Organs and Tissues

| Listed items | Patient's Organs or Tissue to be Treated | Frequency (kHz) ± 1 kHz | Duty cycle (%) ± 5% | Intensity (Lux) ± 10% Lux | Time (minutes) ± 15 seconds |
|---|---|---|---|---|---|
| 3 | Bones | 84 | 74 | 10,175 | 5 |
| 4 | Brain tissue | 78.6 | 74 | 10,175 | 4 |
| 5 | Hair follicles | 80 | 84 | 11,550 | 3 |
| 6 | Ligaments | 83 | 76 | 10,450 | 3 |
| 7 | Lymphatic vessels | 80 | 84 | 11,550 | 3 |
| 8 | Lymph nodes | 76 | 74 | 10,175 | 2 |
| 9 | Muscles | 64 | 84 | 11,550 | 4 |
| 10 | Nail beds | 64 | 80 | 11,000 | 4 |
| 11 | Nerves | 78 | 80 | 11,000 | 4 |
| 12 | Prostate | 80 | 88 | 12,100 | 3 |
| 13 | Ovaries | 72 | 76 | 10,450 | 3 |
| 14 | Testicles | 70 | 84 | 11,550 | 2 |
| 15 | Tendons & fascia | 88 | 88 | 12,100 | 3 |
| 16 | Uterus & Fallopian tubes | 66 | 84 | 11,550 | 4 |

Example 5

Method for Selecting Appropriate Light Therapy

As discussed in Example 1, the addition of the computer enables many different light sequences to be used. The electronics (shown in FIG. 3) can be connected to a light source, such as a LED array (and is not necessarily limited to the LED array of the Parkinson's Light Device 13 of Example 1) to assist in the research into finding the most effective frequencies, intensities, and durations. An example of such an experiment is shown below:

In order to determine a light therapy that is beneficial to a subject, the following steps are used in one embodiment of the method:

1. Select a subject having a condition for which an improvement is desired;
2. Record the subject's condition;
3. Expose the subject to a light with a specified frequency, intensity, and for a specified duration of time;
4. Record the parameters of the light of item (3), above, and record the subject's condition after exposure to the light; and
5. Compare the subject's condition in steps (2) and (4), if the subject's condition has improved after exposure to the light of step (3), then apply the light of step (3) to treat the subject; if the subject's condition has not improved, then repeat steps (1) to (5) using a light of a different frequency, intensity and duration, until a light is found that improves the condition of the subject.

Further, the subject may be exposed to repeated sequences of the light in one sitting (or every few days), to increase his therapeutic light "dosage", and his condition before and after such repeated doses are recorded to determine whether improvement of his condition is found.

Preferably, the user uses software that enables the user to change and save all parameters relating to the light used, such as its frequency, intensity (or duty cycle) and duration. This is useful for the experiments, discussed above, to determine the parameters and duration of the light that is beneficial to a subject.

In one embodiment of the foregoing, as a starting point, the light may be selected from (I) a frequency from about 64 to about 92 kHz; (ii) an intensity of from about 10,037 to about 13,200 Lux; (iii) the subject may be exposed to said light for a duration of time from about 2 minutes to about 6 minutes. Automatic scanning of the subject, by the light device, through the different combinations of the foregoing frequencies, intensities, and durations may be used. If the foregoing ranges of parameters do not produce any beneficial effect, then values outside the ranges may be used. For example, the following parameters may be used (I) a frequency from about 60 to about 95 kHz; (ii) an intensity of from about 9,000 to about 15,000 Lux; and (iii) the subject may be exposed to said light for a duration of time from about 1 minutes to about 7 minutes. If the foregoing ranges still do not produce any beneficial effect, the frequency selected can range from about 5 kHz to about 200 kHz.

The user should preferably begin with super-bright light-sources of very pure green light of about 525 nm peak wavelength. Preferably the Lamina BL-3000 green LED array used in Example 1 is used. More preferably, the Parkinson's Light Device (13) as used in Example 1 is used.

Given the teaching of this patent application, one skilled in the art would realize that other light devices or light sources could be used, in place of the Parkinson's Light Device and light source of Example 1. One skilled in the art would also know how to devise the circuit and programs that would enable the invention herein. Thus, while this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

We claim:

1. A portable light device for treating a subject with light comprising:
    a light source emitting light pulses at a plurality of predetermined intensities, repetition rates, duty cycles and durations, wherein said light source is mounted to direct said light pulses onto said subject; and;
    a controller for modulating the intensities, repetition rates, duty cycles and durations of said light pulses.
    wherein said predetermined pulse repetition rates are stepped in a series of steps between an upper pulse repetition rate chosen between around 92 kHz to around 73 kHz and a lower pulse repetition rate chosen between around 76 kHz to around 64 kHz;
    wherein a particular intensity between around 9000 lux to around 15,000 lux controlled by duty cycle is provided for each of said steps;
    and wherein, each of said steps has a duration of from around 2 minutes to around 6 minutes.

2. The portable light device of claim 1 wherein said light source directs light onto an area of said subject's body, the area being chosen from the group consisting of whole body, partial body and an area of 1 to 10 inches in diameter.

* * * * *